(12) United States Patent
Branch et al.

(10) Patent No.: US 11,896,538 B2
(45) Date of Patent: *Feb. 13, 2024

(54) DEVICE WITH THERAPEUTIC FEATURES

(71) Applicant: ERMI, Inc., Atlanta, GA (US)

(72) Inventors: Thomas P. Branch, Atlanta, GA (US); Edward S. Dittmar, Marietta, GA (US); Timothy James Shary, Atlanta, GA (US); Shaun Kevin Stinton, Sandy Springs, GA (US); Nathaniel K. DeJarnette, Lilburn, GA (US)

(73) Assignee: ERMI, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/290,333

(22) Filed: Mar. 1, 2019

(65) Prior Publication Data

US 2019/0192370 A1 Jun. 27, 2019

Related U.S. Application Data

(63) Continuation of application No. 15/902,237, filed on Feb. 22, 2018, now Pat. No. 10,603,240, which is a
(Continued)

(51) Int. Cl.
*A61H 1/00* (2006.01)
*A61H 1/02* (2006.01)
(Continued)

(52) U.S. Cl.
CPC ............ *A61H 1/008* (2013.01); *A61F 5/0125* (2013.01); *A61F 5/34* (2013.01); *A61H 1/024* (2013.01);
(Continued)

(58) Field of Classification Search
CPC .... A61H 1/008–02; A61H 1/0237–024; A61H 3/00; A61H 2003/007; A61H 9/00;
(Continued)

(56) References Cited

U.S. PATENT DOCUMENTS 4,606,542 A * 8/1986 Segal .................... A61F 5/0125
482/105
5,167,612 A * 12/1992 Bonutti ................. A61F 5/0123
601/33
(Continued)

FOREIGN PATENT DOCUMENTS

EP 1518522 A1 2/2001
WO 99/03440 A1 1/1999

OTHER PUBLICATIONS

Stohr, English translation of WO 99/03440, 1999 (Year: 1999).*
(Continued)

*Primary Examiner* — Justine R Yu
*Assistant Examiner* — Kelsey E Baller
(74) *Attorney, Agent, or Firm* — Shumaker, Loop & Kendrick, LLP

(57) ABSTRACT

Disclosed is a therapeutic stretching apparatus, which in particular provides a user with a system for providing an assist to increase knee extension as well as for maintaining stability of the knee after surgery. This device can not only act as a therapeutic stretching apparatus but also can act as a primary post-op knee brace with locks/limits on hinge to prevent user from further injuring the joint.

13 Claims, 5 Drawing Sheets

Related U.S. Application Data continuation of application No. 13/838,308, filed on Mar. 15, 2013, now Pat. No. 9,931,263.

(51) Int. Cl.
*A61F 5/01* (2006.01)
*A61F 5/34* (2006.01)

(52) U.S. Cl.
CPC .......... *A61F 2005/0172* (2013.01); *A61F 2005/0179* (2013.01); *A61H 2201/0103* (2013.01); *A61H 2201/1238* (2013.01); *A61H 2201/1642* (2013.01); *A61H 2201/1676* (2013.01)

(58) Field of Classification Search
CPC .... A61H 9/005; A61H 9/0078; A61H 9/0092; A61H 2201/0103; A61H 2201/1238; A61H 2201/1642; A61H 2201/1676; A61H 2205/102; A61F 5/0106; A61F 5/012–0125; A61F 5/0144; A61F 5/042; A61F 5/05; A61F 5/05816–05825; A61F 5/34; A61F 2005/0153; A61F 2005/0158
See application file for complete search history.

(56) References Cited

U.S. PATENT DOCUMENTS

| | | |
|---|---|---|
| 5,213,094 A | 5/1993 | Bonutti |
| 6,669,660 B2 | 12/2003 | Branch |
| 6,872,186 B2 | 3/2005 | Branch et al. |
| 7,479,121 B2 | 1/2009 | Branch |
| 7,500,957 B2 | 3/2009 | Bledsoe |
| 7,547,289 B2 | 6/2009 | Branch |
| 8,012,108 B2 * | 9/2011 | Bonutti .................. A61F 5/013 601/5 |
| 9,669,249 B2 | 6/2017 | Marti et al. |
| 9,873,010 B2 | 1/2018 | Marti et al. |
| 10,220,234 B2 | 3/2019 | Marti et al. |
| 10,293,198 B2 | 5/2019 | Marti et al. |
| 10,966,854 B1 * | 4/2021 | Lockart .............. A63B 21/0407 |
| 2012/0089065 A1 | 4/2012 | Pflaster et al. |
| 2012/0271211 A1 | 10/2012 | Bledsoe |
| 2013/0041300 A1 | 2/2013 | Nace |
| 2014/0005583 A1 | 1/2014 | Cardinali |
| 2017/0027735 A1 * | 2/2017 | Walsh .................. A61F 5/0102 |
| 2019/0111299 A1 | 4/2019 | Radcliffe et al. |

OTHER PUBLICATIONS

International Searching Authority, ISR and Written Opinion for International Application No. PCT/US2014/026309, dated Jun. 4, 2014, 13 pages, EPO, The Netherlands.

* cited by examiner

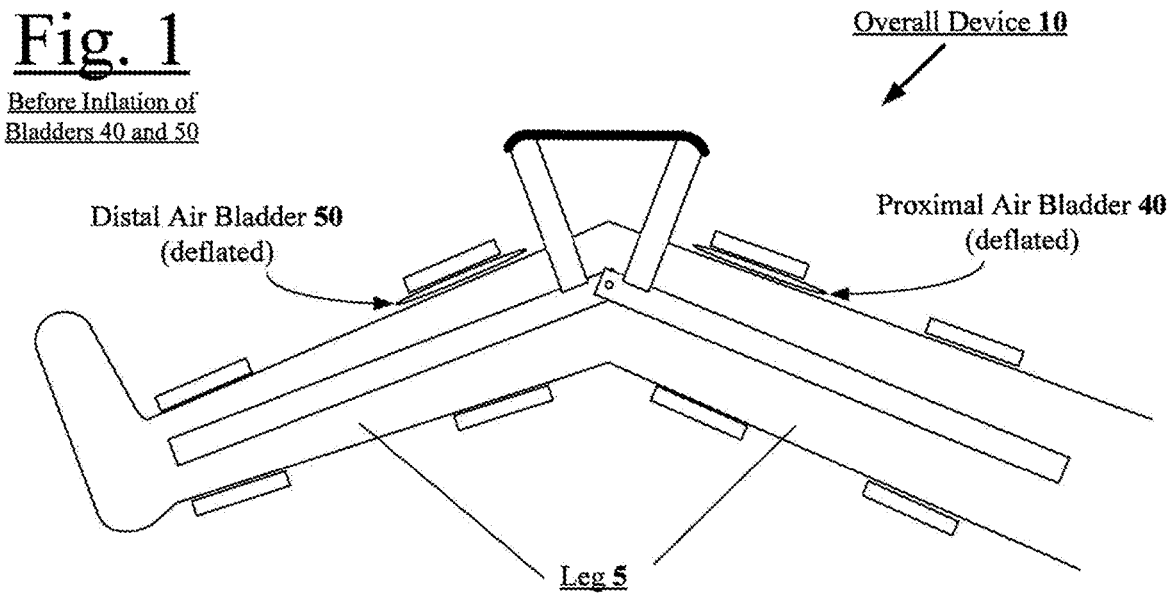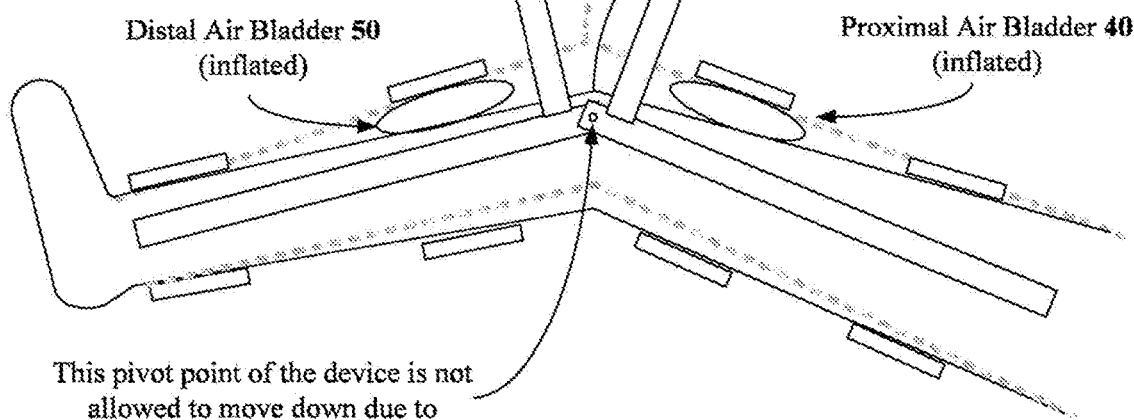

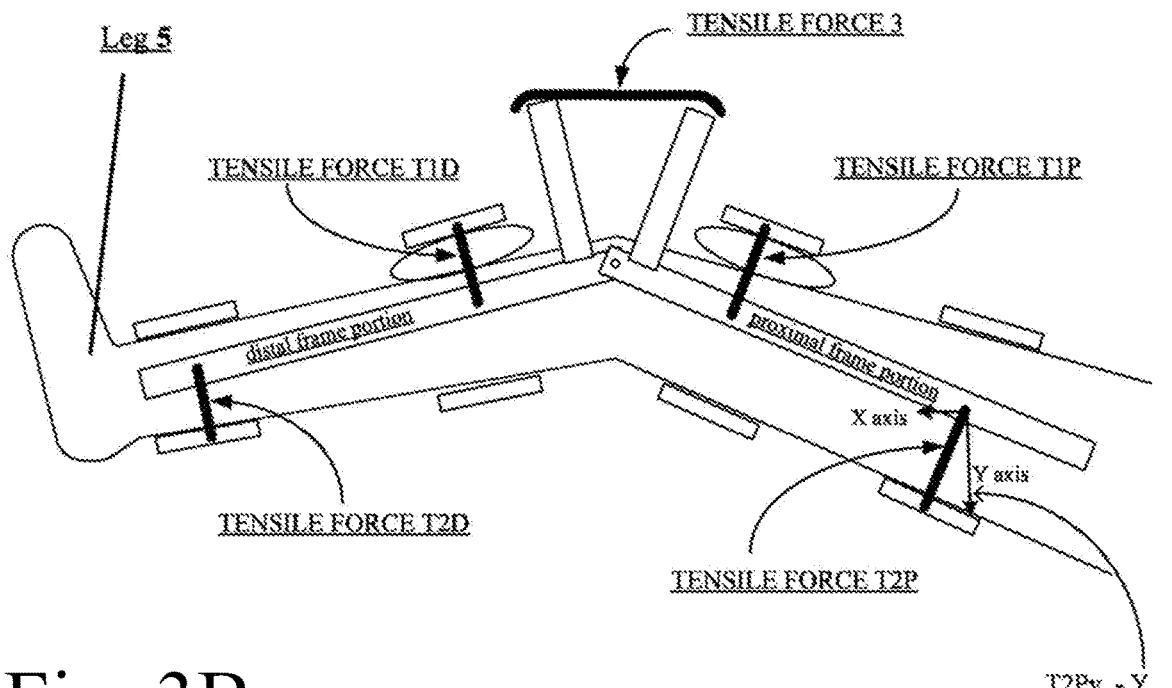

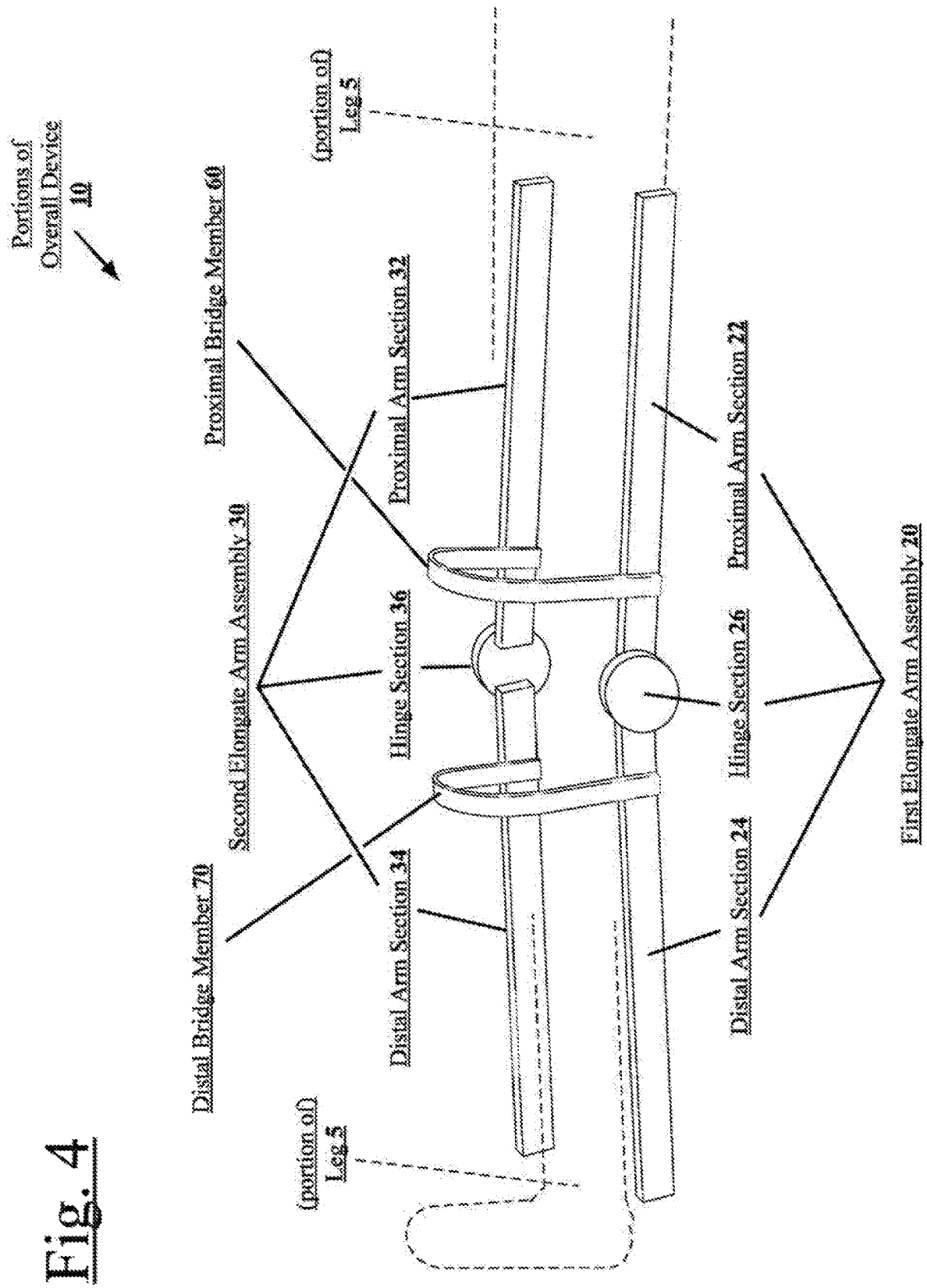

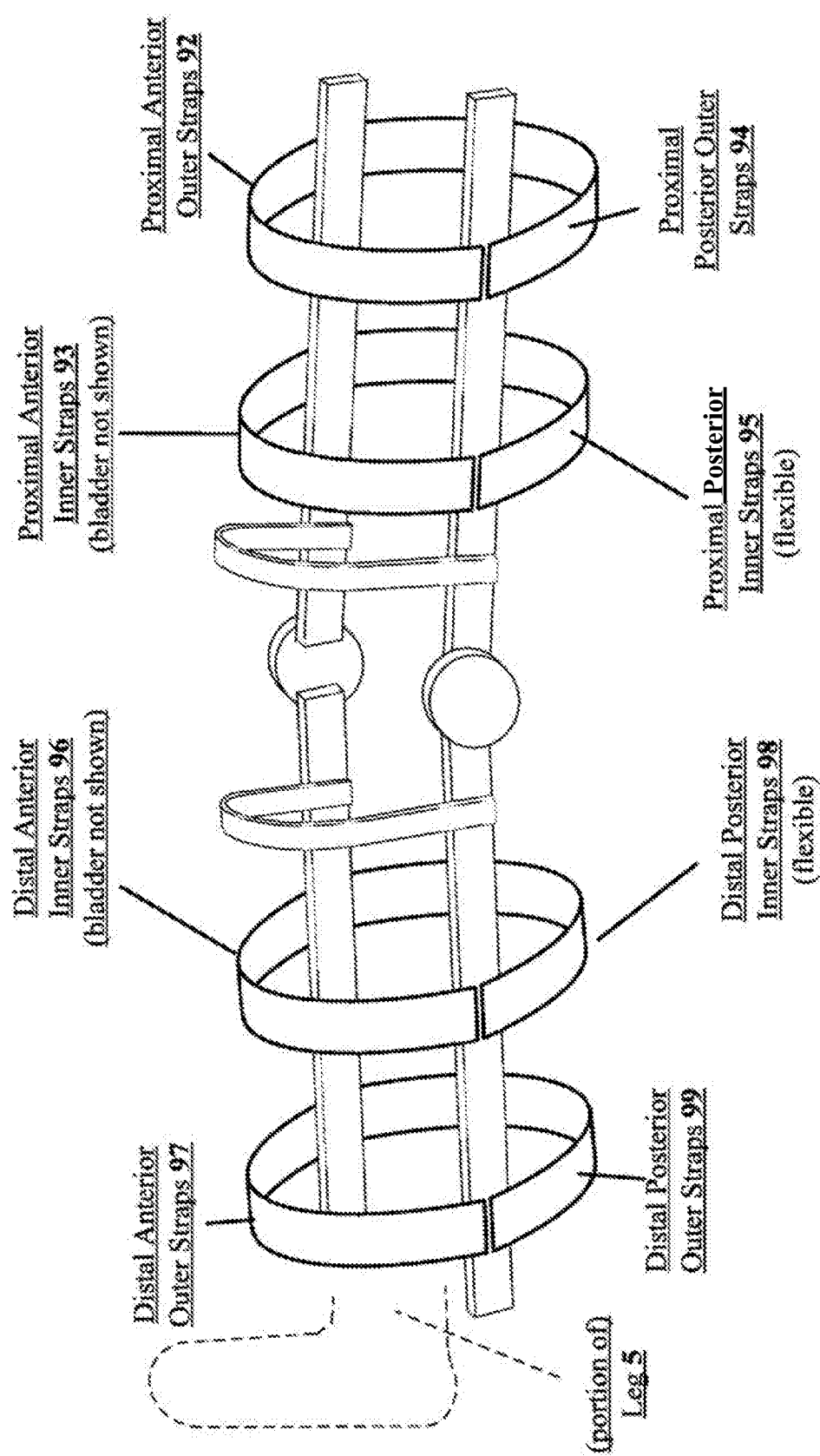

DEVICE WITH THERAPEUTIC FEATURES

CROSS-REFERENCE TO RELATED APPLICATIONS

This application claims priority to and the benefit of U.S. patent application Ser. No. 15/902,237 filed Feb. 22, 2018, which is a Continuation of U.S. patent application Ser. No. 13/838,308, filed Mar. 15, 2013, now U.S. Pat. No. 9,931,263 issued Apr. 3, 2018 entitled "Device with Therapeutic Features," which is hereby incorporated herein in their entireties.

BACKGROUND

Technical Field

The present invention related to the field of therapeutic treatment of joints, such as needed after surgery.

Description of Related Art

Prior art therapeutic devices are well known in the art. An example is of the inventors own concepts such as shown in U.S. Pat. Nos. 6,669,660, 6,872,186, 7,479,121, 7,547,289, each of which is expressly incorporated by reference herein, and others. However, improvements are always welcomed.

BRIEF SUMMARY OF VARIOUS EMBODIMENTS OF THE INVENTION

According to various embodiments of the present invention, a therapeutic device is provided for use on a length of a user's leg, the length including an upper leg portion, a lower leg portion, and a knee intermediate the two, the leg length also defining opposing proximal and distal sides each extending the length of the leg length, the device comprising: a proximal framework portion configured for attachment relative to the upper leg portion, the proximal framework portion including a leg facing portion configured to be directed towards and generally facing the proximal side of the upper leg; a distal framework portion configured for attachment relative to the lower leg portion, the proximal framework portion including a leg facing portion configured to be directed towards and generally facing the proximal side of the upper leg; at least one pivoting connection intermediate and connecting the proximal and distal framework portions, the pivoting connection configured to facilitate pivoting of the proximal and distal framework portions in device flexion such as when the device is attached to the leg and leg is in flexion and the proximal and distal framework portions can pivot relative to each other; a connector configured to selectively connect the proximal and distal framework portions so as to selectively discourage device flexion of the proximal and distal framework upper frame member relative to the lower frame member; and at least one selectively inflatable bladder between the proximal side of the leg and one of the proximal and distal framework portions, in particular between the proximal side of the leg and the corresponding leg facing portion of the one of the proximal and distal framework portions, the elements above configured to interact such that inflation of the bladder while the connector is connected causes the leg to be urged into extension due to the pushing of the bladder against the proximal side of the leg.

The device above may include the leg facing portion of the one of the proximal and distal framework portions as a strap configured to be placed in tension.

The device above may include the connector as an elongate tensile connector having each end attached to one of the proximal and distal framework portions.

The device above may include the connector including a ratchet capability configured to take up the length of the elongate tensile connector.

The device above may include the connector as a one-way ratchet configuration proximate the pivoting connection.

The device above may include the framework portion including a strap configured for attachment relative to the upper leg.

The device above may include one of the proximal and distal framework portions including an elastic strap in contact with the anterior side of the leg at approximately the same length at which the bladder is in contact to the proximate side.

The device above may include at least one bladder being a first bladder, and further comprising a second bladder between the proximal side of the leg and the other of the proximal and distal framework portions, in particular between the proximal side of the leg and the corresponding leg facing portion of the other of the proximal and distal framework portions.

The device above may include the other of the proximal and distal framework portions also including an elastic strap in contact with the anterior side of the leg at approximately the same length at which the second bladder is in contact to the proximate side.

According to various embodiments of the present invention, a therapeutic device is provided for use on a length of a user's leg, the length including an upper leg portion, a lower leg portion, and a knee intermediate the two, the leg length also defining opposing proximal and distal sides each extending the length of the leg length, the device comprising: A) a proximal device portion itself comprising: 1) a proximal framework portion configured for attachment relative to the upper leg portion, the proximal framework portion including a leg facing portion configured to be directed towards and generally facing the proximal side of the upper leg; and 2) an inflatable proximal bladder between the proximal side of the leg and the proximal framework portion, in particular between the proximal side of the leg and the corresponding leg facing portion of the proximal framework portion; B) a distal device portion itself comprising: 1) a distal framework portion configured for attachment relative to the lower leg, the proximal framework portion including a leg facing portion configured to be directed towards and generally facing the proximal side of the upper leg; and 2) an inflatable distal bladder between the distal side of the leg and the distal framework portion, in particular between the proximal side of the leg and the corresponding leg facing portion of the distal framework portion; C) at least one pivoting connection intermediate and connecting the proximal and distal device portions, the pivoting connection configured to facilitate pivoting of the proximal and distal device portions in device flexion such as when the device is attached to the leg and leg is in flexion and the proximal and distal device portions can pivot relative to each other; and D) a connector configured to selectively connect the proximal and distal framework portions so as to selectively discourage device flexion of the proximal and distal device members relative to each other, the elements above configured to interact such that inflation of the proximal and distal bladders while the connector is connected causes the leg to be urged into extension due to the pushing of the bladders against the proximal side of the leg.

The device above may include each leg facing portion of each of the one of the proximal and distal framework portions being a strap configured to be placed in tension.

The device above may include the connector as an elongate tensile connector having each end attached to one of the proximal and distal framework portions.

The device above may include the connector including a ratchet capability configured to take up the length of the elongate tensile connector.

The device above may include the connector as a one-way ratchet configuration proximate the pivoting connection.

The device above may include the framework portion including a strap configured for attachment relative to the upper leg.

The device above may include one of the proximal and distal framework portions including an elastic strap in contact with the anterior side of the leg at approximately the same length at which the bladder is in contact to the proximate side.

According to various embodiments of the present invention, a method is provided for providing therapeutic motion to a length of a user's leg, the length including an upper leg portion, a lower leg portion, and a knee intermediate the two, the leg length also defining opposing proximal and distal sides each extending the length of the leg length, the method comprising: A) providing a device which will tend to immobilize the length of a user's leg so as to discourage extension; B) selectively modifying the device such that the length of a user's leg moves in extension to a first predetermined limit; and C) urging a portion of the length of the user's leg relative to a portion of the device via an inflatable bladder pushing against the proximal side of the leg, such that the length of the user's leg moves in further extension past the first predetermined limit; D) deflating the inflatable bladder such that the length of the user's leg moves in flexion back to approximately the first predetermined limit; and E) again urging the portion of the length of the user's leg relative to a portion of the device via an inflatable bladder such that the length of the user's leg moves in further extension past the first predetermined limit a second time.

According to various embodiments of the present invention, method is provided for providing therapeutic motion to a length of a user's leg, the length including an upper leg portion, a lower leg portion, and a knee intermediate the two, the leg length also defining opposing proximal and distal sides each extending the length of the leg length, the method comprising: A) providing a pivoting brace having two parts, and upper part and a lower part, the upper and lower parts being pivotably connected and configured to move in flexion and extension along with the movement of the length of the user's leg in corresponding flexion and extension; B) moving the user's leg in extension to a first extended position such that the brace moves in extension along with the leg, with the upper part of brace moving in extension relative to the lower part of the brace; C) preventing further extension of the upper part of brace relative to the lower part of the brace; D) urging a portion of the length of the user's leg relative to a portion of the device such that the length of the user's leg moves in further extension past the first predetermined limit; D) deflating the inflatable bladder such that the length of the user's leg moves in flexion back to approximately the first predetermined limit; and E) again urging the portion of the length of the user's leg relative to a portion of the device via an inflatable bladder such that the length of the user's leg moves in further extension past the first predetermined limit a second time.

According to various embodiments of the present invention, method is provided for providing therapeutic motion to a length of a user's extremity, the length including an upper extremity portion, a lower extremity portion, and a joint intermediate the two, the extremity length also defining opposing proximal and distal sides each extending the length of the extremity, the method comprising: A) providing a pivoting brace having two parts, and upper part and a lower part, the upper and lower parts being pivotably connected and configured to move in flexion and extension along with the movement of the length of the user's extremity in corresponding flexion and extension; B) moving the user's extremity in extension to a first extended position such that the brace moves in extension along with the extremity, with the upper part of brace moving in extension relative to the lower part of the brace; C) preventing further extension of the upper part of brace relative to the lower part of the brace; D) urging a portion of the length of the user's extremity relative to a portion of the device such that the length of the user's extremity moves in further extension past the first predetermined limit; D) deflating the inflatable bladder such that the length of the user's extremity moves in flexion back to approximately the first predetermined limit; and E) again urging the portion of the length of the user's extremity relative to a portion of the device via an inflatable bladder such that the length of the user's extremity moves in further extension past the first predetermined limit a second time.

BRIEF DESCRIPTION OF THE SEVERAL VIEWS OF THE DRAWING(S)

FIG. 1 is an exemplary drawing showing the overall device according to one embodiment of one of the inventions herein, attached to an exemplary leg 5. Also numbered are distal air bladder 50 and proximal air bladder 40. These two bladders are shown in a relatively deflated configuration.

FIG. 2 is an exemplary drawing similar to FIG. 1, except that the proximal air bladder 40 and the distal air bladder 50 are inflated. The previous leg position of FIG. 1 is shown here in dotted line.

FIG. 3A is an illustrative static force diagram generally showing various static forces, torques and their directions on the device and the leg, at a given inflation of the bladders; and FIG. 3B is a table illustrating calculations and assumptions associated with force and torque of the device.

Figure 6:
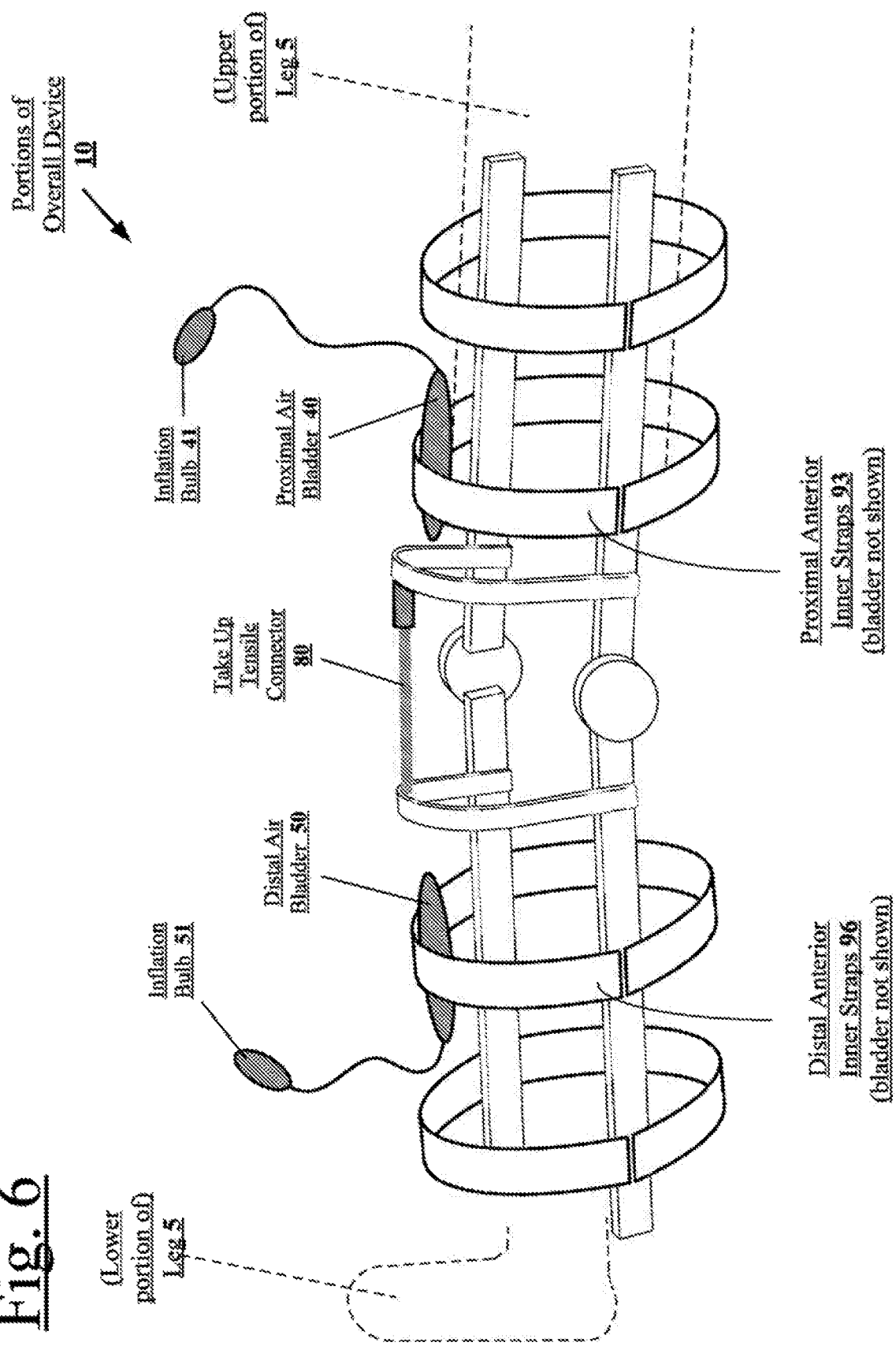

FIG. 4 is an illustrative diagram showing portions of the overall device 10 (namely the first and second elongate arm assemblies 30 and 40, respectively, and the proximal and distal bridge members 60, 70, respectively. A portion of the leg 5 is also shown in phantom.

FIG. 5 is an illustrative diagram showing the portions of the overall device 10 of FIG. 4, but also the four straps of the strap collection.

FIG. 6 is an illustrative diagram showing the portions of the overall device 10 of FIG. 5, but also the proximal air bladder 40 and its inflation bulb 41, the distal air bladder 50 and its inflation bulb 51, and the take up tensile connector.

DETAILED DESCRIPTION OF VARIOUS EMBODIMENTS

Various embodiments of the present invention will now be described more fully hereinafter with reference to the accompanying drawings, in which some, but not all embodiments of the invention are shown. Indeed, embodiments of the invention may be embodied in many different forms and should not be construed as limited to the embodiments set forth herein. Rather, these embodiments are provided so that this disclosure will satisfy applicable legal requirements. Unless otherwise defined, all technical and scientific terms used herein have the same meaning as commonly known and understood by one of ordinary skill in the art to which the invention relates. The term "or" is used herein in both the alternative and conjunctive sense, unless otherwise indicated. Like numbers refer to like elements throughout.

Note that when the term "invention" is used herein, it is not necessarily used to identify a single isolated concept, but could in fact be identifying a plurality of concepts, and should not in any way be construed as limiting any available coverage afforded any patent issuing from this application to a single concept. Said another way, when the phrase "the invention" is used, it should be understood that this could include a multiple set of inventions, each of which could be separately and independently patented or otherwise protected.

Outline
Overview
Element List
General Construction and Operation
More Detailed Discussion
  Overall Device
  First and Second Elongate Arm Assemblies
  Proximal and Distal Air Bladders
  Take-Up Tensile Connector
  Strap Collection
  Methods For Use—Therapeutic and Brace Modes
  Alternate Description of Elements
  Materials
  Options and Alternatives
Conclusion Overview This invention relates generally to therapeutic stretching apparatus, and in particular provides a user with a system for providing an assist to increase joint extension as well as for maintaining stability of the joint after surgery. As an example, a system is shown which increases knee extension as well as for maintaining stability of the knee after surgery. This device can not only act as a therapeutic stretching apparatus but also can act as a primary post-op knee brace with locks/limits on hinge to prevent user from further injuring the joint.

Other joints should be understood as being capable of manipulation under the present inventions, including but not limited to the elbow, shoulder, finger joints, ankle, etc.

ELEMENT LIST

5 Exemplary leg (or portion thereof)
10 Overall device
  20 First elongate arm assembly
    22 Proximal arm section
    24 Distal arm section
    26 Hinge section (aka Hinge 26)
  30 Second elongate arm assembly
    32 Proximal arm section
    34 Lower arm section
    36 Hinge section (aka Hinge)
  40 Proximal Air Bladder
    41 Quick-Release Inflation Bulb
  50 Distal Air Bladder
    51 Quick-Release Inflation Bulb
  60 Proximal bridge member
  70 Distal bridge member
  80 Take-up Connector
  90 Strap Collection
    92 Proximal anterior outer straps—high tensile strength fabric
    93 Proximal anterior inner straps—high tensile strength fabric plus bladder
    94 Proximal posterior outer straps—high tensile strength fabric
    95 Proximal posterior inner straps—flexible
    96 Distal anterior inner straps—high tensile strength fabric plus bladder
    97 Distal anterior outer straps—high tensile strength fabric
    98 Distal posterior inner straps—flexible
    99 Distal posterior outer straps—high tensile strength fabric General Construction and Operation This device provides the user with a system for providing an assist to increase knee extension as well as for maintaining stability of the knee after surgery. This device can not only act as a therapeutic stretching apparatus (while in its "therapeutic mode") but also be used in a "brace mode", in which it acts as a primary post-op knee brace with locks/limits on the hinge to prevent the user from further injuring the joint.

The general construction includes two elongate arm assemblies 20, 30, each of which extend down opposite sides of the user's leg. Each of these assemblies includes a pivot element which is preferably aligned with the user's knee joint when pivoting. The two assemblies are linked together by "U"-shaped proximal and distal bridge members 60, 70, providing a substantially rigid connection therebetween, while still allowing the two pivot elements to pivot while in brace mode. In therapeutic mode, a take up tensile connector connects the two bridge members; then the proximal and distal air bladders 40, 50, are inflated so as to provide a therapeutic action as discussed in later detail.

More Detailed Discussion

Overall Device
The overall device 10 according to one embodiment of the present invention is shown in FIGS. 1-6.
The device 10 includes the following subelements:
First elongate arm assembly 20 (extends down one side of leg)
Second elongate arm assembly 30 (extends down other side of leg)
Proximal Air Bladder 40 (positioned atop thigh, to move femur)
Distal Air Bladder 50 (positioned atop shin, to move tibia)
Proximal Bridge Member 60 (spans assemblies 20 and 30)
Distal Bridge Member 70 (spans assemblies 20 and 30)
Take Up Tensile Connector 80 (connects bridge members 60 and 70)
Strap Collection 90 (includes multiple straps)

First and Second Elongate Arm Assemblies 20, 30
The general "framework" of the device (the part providing relatively rigid structure) consists of two hinged/jointed arm assemblies 20, 30, with locations for the straps to attach.
Each of these arm assemblies 20, 30, is generally similar to the other, except that they are the minor image of the other, as each fits on one side of the leg of the user. Although the device 10 may be used with either leg, it will be assumed for discussion that it is being used on the left leg. Assuming this to be the case, the first elongate arm assembly 20 would be positioned along the left side of the leg 5 as shown in FIG. 4. Similarly, the second elongate arm assembly 30 would be positioned along the right side of the leg 5.

Each assembly includes a proximal arm section, a distal arm section, and a hinge section intermediate and connecting the two. Proximal arm sections are configured to be positioned adjacent to and attached relative to the proximal portion of the leg (the portion including the femur); Distal arm sections are configured to be positioned adjacent to and attached relative to the distal portion of the leg (the portion including the tibia). The hinge section is configured to provide a hinge function, as least in one operational mode of the device 10.

First arm assembly 20 includes a proximal arm section 22, a distal arm section 24, and a hinge section 26 intermediate and connecting the proximal and distal arm sections 22, 24.

Second arm assembly 30 includes a proximal arm section 32, a distal arm section 34, and a hinge section 36 intermediate and connecting the proximal and distal arm sections 32, 34.

The hinge sections 26, 36, (aka "hinges") are in one inventive embodiment configured to provide a pivoting connection between their associated proximal and distal arm sections. These hinges could have a variety of options. For example they could be configured to have two selectable modes—a completely locked mode and a completely free mode, the former providing a selectable rigid connection between the associated proximal and distal arm sections, and the latter providing complete pivoting without stops. Another option could also include an additional "pivot range" mode in which "stops" or "limits" could be provided that would preclude flexion or extension of the knee outside a certain range of pivot motion. The stop or limits could be adjustable as needed.

Proximal and Distal Air Bladders 40, 50

During the use of the device 10 in its therapeutic mode, the proximal and distal air bladders 40, 50, are inflated and deflated through the use of a manual pumping mechanism. This could be done independently, for a personalized application of force to the limb, or at the same time if the same bulb is connected to both bladders. In the drawings, proximal air bladder 40 is inflated and deflated via quick release inflation bulb 41, and distal air bladder 50 is inflated and deflated via quick release inflation bulb 51. As discussed later, proximal air bladder 40 is attached to corresponding proximal anterior inner strap 93, which is itself attached to the frame of the device 10. Similarly, distal air bladder 50 is attached to corresponding distal anterior inner strap 96, which is itself attached to the frame of the device 10.

As the air bladders are inflated during the therapeutic mode of the device, the bladders expand between the corresponding straps and the leg of the user, causing the leg of the user to be urged along the working tensile length portions of the straps, thus urging the knee of the leg into extension as shown in FIGS. 1 and 2.

As discussed in later detail, during therapeutic use of the device 10, when the proximal air bladder 40 is inflated and deflated via quick release inflation bulb 41, bladder 40 tends to move the femur relative to the overall framework of the device 10. When the distal air bladder 50 is inflated and deflated via quick release inflation bulb 41, bladder 50 tends to move the tibia relative to the overall framework of the device 10. Due to the positioning of other straps intermediate the leg and the framework of the device, such inflation causes the femur and tibia to be moved relative to each other such that the intermediate knee is urged into greater extension as discussed in later detail.

Proximal and Distal Bridge Members 60, 70

As shown in FIG. 4, the proximal and distal bridge members 60, 70, are similar in their "U"-shaped construction, and each span from one elongate assembly 20 to the other assembly 30, providing a substantially rigid connection therebetween.

The proximal bridge member 60 is rigidly attached at one end to the proximal arm section 22 of the first elongate arm assembly 20, and attached at its other end to the proximal arm section 32 of the second elongate arm assembly 20.

The distal bridge member 70 is rigidly attached at one end to the distal arm section 24 of the first elongate arm assembly 20, and attached at its other end to the distal arm section 34 of the second elongate arm assembly 20.

Take-Up Tensile Connector 80

Referring now particularly to FIG. 6, the take-up tensile connector 80 is configured to connect the proximal bridge member 60 to the distal bridge member 70 when the device 10 is in its therapeutic mode. One end of the connector 80 attaches to member 70 and the other end attaches to member 80.

When the connector 80 is in place, it discourages flexion yet allows extension of the knee, by discouraging "device flexion" and allowing "device extension" of the proximal and distal subassemblies PFP, DFP (aka upper and lower frame subassemblies). "Device flexion" shall be understood as the relative movements of the upper and lower frame subassemblies when the leg is in flexion when the device is used as a pivoting brace, and "device extension" shall be understood as the relative movements of the upper and lower frame subassemblies when the leg is in extension when the device is used as a pivoting brace.

The connector includes a take-up feature which allows the connector to be reduced in length while being connected to the proximal bridge member 60 and distal bridge member 70. This reduction in length or "contraction" is used to urge the medial portions of the proximal bridge member 60 and distal bridge member 70 towards each other, causing the brace to move such that the knee is urged into extension as much as possible, prior to the use of the balloons as discussed elsewhere.

When the buckle/ratchet and strip are not engaged they will rotate/pivot out of the way so as not to hinder the user from walking around while the apparatus is used as a conventional brace.

In one configuration, the take-up tensile connector 80 is in the form of a buckle/ratchet mechanism and semi-rigid strip; with the buckle/ratchet being secured to the proximal bridge member 60 and the strip secured to the distal bridge member 70. The connector 80 can be in the form of a ratchet/buckle having a lever arm on the upper rigid support such that when lifted it moves the strip attached to the lower rigid support towards the upper support. When the lever arm is lowered it holds the strip in its current location. Under one configuration, there is a semi-rigid strip that is rigid enough to be pushed through a slot in the other connector portion, the slot having a ratchet element, such that if the brace is pivoted by the user (such as by the user sitting on the floor and pushing down on the anterior side of it), the ratchet effect takes place automatically. In this situation, the user could slip the toothed semi-rigid strip into the ratcheted slot, and then push down on the brace (against or with the assistance of the leg)

so that the take-up tensile connector is shortened. However, other configurations performing similar functions are likewise contemplated.

Strap Collection 90

There are multiple separate straps to secure the brace to the leg; ideally four anterior and four posterior straps. Referring now in particular to FIG. 5, this "strap collection" 90 includes a plurality of straps listed as follows:

Proximal anterior outer straps 92—high tensile strength fabric

Proximal anterior inner straps 93—high tensile strength fabric [attached to bladder]

Proximal posterior outer straps 94—high tensile strength fabric

Proximal posterior inner straps 95—flexible

Distal anterior inner straps 96—high tensile strength fabric [attached to bladder]

Distal anterior outer straps 97—high tensile strength fabric

Distal posterior inner straps 98—flexible

Distal posterior outer straps 99—high tensile strength fabric

Note that a single strap could be used for any one of the above "straps", wound around and turned back as necessary in order to use a single piece of strapping. "Strap" and "straps" are thus used interchangeably (e.g., strap 92 or straps 92). Other flexible materials, in one piece or otherwise, are likely contemplated.

Within the collection 90, the straps for the proximal and distal ends of the brace, on both anterior and posterior sides, are in one embodiment of a flexible construction including high tensile strength, (such as a fabric like nylon, polypropylene, polyester webbing or the like) and provide the primary "rigid" (in the tensile direction) attachment of the brace to the leg. As shown in FIG. 5, these straps are the following:

Proximal anterior outer straps 92—high tensile strength fabric Proximal posterior outer straps 94—high tensile strength fabric Distal anterior outer straps 97—high tensile strength fabric Distal posterior outer straps 99—high tensile strength fabric Within the strap collection 90, on the posterior side of the brace, towards the middle of the brace but not on the joint, include elastic straps (such as webbing with suitable rubber strands or the like in the tensile direction) to allow the knee to move relative to the brace during therapeutic use of the device 10, while still providing a suitable urging force upon the anterior side of the leg during use as a brace. As shown in FIG. 5, these straps are the following:

Proximal posterior inner straps 95—flexible

Distal posterior inner straps 98—flexible

Within the strap collection 90, anterior middle straps will contain the air bladders and be comprised of the same or other suitable similar high tensile strength fabric material. They attach to and support the air bladders in such a way that allows the bladder to be sandwiched between the fabric strap and the user's leg. These include the following straps:

Proximal anterior inner straps 93—high tensile strength fabric [attached to bladder]

Distal anterior inner straps 96—high tensile strength fabric [attached to bladder]

Methods for Use: Therapeutic Mode and Brace Mode

Under one embodiment of one invention disclosed herein, the device 10 may be used in two different modes: "therapeutic mode" and "brace mode". The device may be used in only one of said modes, or may be used alternately in either mode, with or without removal in between modes.

In therapeutic mode, the device 10 may be used in a particular manner in order to provide advantageous therapeutic stretching or the like of certain aspects of the user's body. In particular, the brace may be used to provide increased knee extension in a selectively and predetermined controlled environment, such as is often needed after knee surgery or the like.

In brace mode, the device 10 may be used in order to provide a more traditional brace function, that being to provide structural assistance to support the knee or adjacent parts of the leg, provide limits on flexion and/or extension of the leg in order to preclude further injury, and as a post-operative brace support system to protect the leg and prevent unexpected injury during the vulnerable post-operative period when the patient lacks pain control and muscle control.

For either mode, installation and removal of the device to and from the leg is essentially the same. For installation, typically the hinges 26, 36 are set to move freely enough to allow the device to be installed. The device 10 is then attached to the intended leg via the various straps in the strap collection 90. Each of the four distal straps are attached to the distal part of the leg as shown in the various figures, as are the four proximal straps attached to the proximate part of the leg, such that the two hinges 26, 36 are on either side of the knee, with the hinge axes preferably aligning with the axis of the knee joint.

Should the user then elect to use the device 10 in therapeutic mode, in one embodiment of the invention the user removes any restrictions from the hinges, i.e. locks and limits, before beginning the process. Once all locks/limits are removed/disengaged from the hinges, the user then extends his/her knee as far as possible, and then engages and retracts the take-up tensile connector as much as possible without experiencing significant pain. In one embodiment, the user is instructed to retract the take-up tensile connector until the user just begins to feel an extension stretch in the knee.

At this point, the deflated air bladders 40, 50, are then inflated via manual operation of the corresponding inflation bulbs 41, 51, from for example the deflated condition of FIG. 1 to the inflated condition of FIG. 2. As may be seen, the bladders, both being on the anterior side of the leg, will begin to press the knee into more extension, providing a desired stretching process. The take up tensile connector 80 will be placed in ever increasing tension during this inflation process.

Thus it may be understood that when the patient uses the brace to stretch his knee into extension, in one inventive embodiment he must first lock the two rigid anterior proximal and distal bridge members together with a ratchet strap. The ratchet strap is then levered a number of times to close the gap between the proximal and distal bridge members until the patient just begins to feel an extension stretch in the knee. At this point, the patient uses the bulb and bladder system to perform the final intermittent stretching protocol of inflation and deflation to cause the final extension stretch of the knee. The formal protocol can be modified by the patient; one suggestion is a stretching program duration of 10 minutes per session at frequency of 6 sessions per day.

An exemplary showing of the general forces, torques and their directions on the device 10 and the leg is shown in FIG. 3. As shown in in FIG. 3, for a given axis, (e.g., the Y axis) As may be understood, in a given axis, for example, the x axis:

$$T_1P_y + T_1D_y = T_2P_y + T_2D_y$$

Assuming that all four tensile forces are approximately equal, clockwise torque exists on the proximal frame portion, and counterclockwise torque exists on the distal frame portion. Thus there will be positive tension in the take-up tensile member, having a value of "Tensile Force 3".

Note that the user can at any time terminate such balloon-induced stretching by releasing the compressed air within the inflation bulbs 41, 51. In one embodiment of one invention, bulbs have "quick-release" buttons are used so as to allow the user to quickly release the pressure should too much pain be encountered.

After the desired stretch is complete, the air is released from the bladders 40, 50, and the take up tensile connector 80 is disconnected.

The device is then ready to be either removed, or placed in brace mode. Removal is readily accomplished by disengaging the various straps in the strap collection 90 from the leg.

If it is desired to put the device 10 into brace mode, the take up tensile connector 80 is suitably secured in an out of the way disengaged configuration. The hinges 26, 36, are then set as needed to provide the brace effect as needed. In one embodiment, the hinges could be completely locked; this might be a good setting immediately following surgery. The hinges could then be adjusted as known in the art to provide a desired range of pivoting motion with finite "stops" precluding flexion or extension of the knee past a certain range.

Alternate Description of Elements

It may be understood that the interconnections of the proximal and distal bridge members 60 and 70 with the first and second elongate arm assemblies 20 and 30 provide in effect two relatively pivoting proximal and distal framework portions, each of which are configured to attach to leg. The proximal framework portion (not labeled in the drawings, but referenced in this text as "PFP") include the proximal arm section 22, the proximal arm section 32, the proximal bridge member 60, and the proximal straps 92, 93, 94, and 95. The distal framework portion (not labeled in the drawings, but referenced in this text as "DFP") include the distal arm section 24, the distal arm section 34, the distal bridge member 70, and the distal straps 96, 97, 98, and 99. These relatively pivoting proximal and distal framework portions PFP and DFP pivot via at least one pivoting connection, in the drawings shown through the intermediate hinge sections 26, 36, which preferably have substantially common pivot axes (when they are so free to pivot).

These proximal and distal framework portions PFP and DFP could be thought of as being part of larger proximal and distal device portions, with each device portion including a framework portion and a bladder. These proximal and distal device portions likewise pivot via at least one pivoting connection, in the drawings shown through the same intermediate hinge sections 26, 36, which preferably have substantially common pivot axes (when they are so free to pivot).

Said another way, the "Proximal Device Portion" (not labeled in the drawings but referenced in this text as "PDP") includes the proximal framework portion PFP, and the proximal bladder 40. Similarly, the "Distal Device Portion" (not labeled in the drawings but referenced in this text as "DDP") includes the distal framework portion DFP, and the distal bladder 50. The proximal and distal device portions pivot via the two hinge sections 26, 36, when so free to pivot.

The proximal and distal framework portions could also be known as "upper and lower framework portions", "proximal and distal frame portions", "upper and lower frame portions", or other suitable terms.

The proximal and distal device portions PFP and DFP could also be known as "upper and lower device portions", or other suitable terms.

Materials

In one embodiment, the frame assemblies 20, 30, could be made of various materials, including aluminum, steel, titanium or other metal alloys, carbon fiber or other fiber enhanced plastic, wood, or other suitably rigid metals, plastics, or other materials.

In one embodiment, the "high tensile" straps 92, 93, 94, 96, 97, and 99 could be made of fabric webbing such as nylon, polypropylene, polyester webbing or the like. The more elastic straps 95 and 98 could be made of elastic straps (such as webbing with suitable rubber strands or the like in the tensile direction).

Options and Alternatives

Note that multiple bladders could be used in place of a single bladder mentioned above, as appropriate. Any inflator device could be used, although in one embodiment a quick release of air feature is desired to allow the user to quickly reduce pressure in case of pain.

Note that both bladders 40, 50, mentioned above could be pumped by same bulb, either at the same time, or individually by allowing the bulb to be selectively attached to either bladder as needed or by appropriate valving. Each bladder could be inflated separately/individually or together at varying rates and pressures. The bulb system could be incorporated into the structure of the bladder or brace like the integral air pump in e.g., some Nike® or Reebok® shoes.

While the device is in brace mode, the bladders could be left in place in their deflated state between the leg and the proximate strap, or the bladders could be removed as desired.

The air bladders may be inflated manually by air bulbs; either through a tube running from the bag to the bulb or from inserting the bulb directly into the bag.

Note that the hinge sections 26, 36, (aka "hinges") could provide not only the functions described above (complete locking, completely free pivoting, selected range pivoting), but they could also be additionally configured to include a "ratchet" mode, which would provide a function similar to the ratcheting Take Up Tensile Connector 80 also mentioned above, which would obviate the need for the connector (the hinge would be put into a ratchet mode that would allow for one-way pivoting of the device in the "device extension" direction (prior to use of the bladders).

In the description above, the flexible posterior straps 95 and 98 are stretchable, so as to provide a bias on the posterior side of the leg. It should be understood that such a strap configuration could include a feature to allow for snugging up with a second, parallel, non-stretching strap to provide for more structural support during brace mode. Also, a number of different straps could be used, i.e., each strap could have different material properties with a range from stiff to elastic. The system would be changed by replacing a strap with one more elastic or stiff. Such a strap could also have an elastic segment AND a stiff segment. The stiff segment could be attached to the front of the stays of the brace and the elastic segment could be attached to the back of the stays of the brace. Thus, the thigh or leg could stretch backwards out of the brace but not forward.

Another variation of straps 95 and 98 could include use of a fully rigid strap with an elastic portion that spans like a chord across one segment of the strap. Thus, the elastic portion would initially engage the limb, but the rigid portion would come into play when the elastic strap bottoms out on the rigid strap. Alternately, straps 95 and 98 could be replaced temporarily by a stiff strap when the device is used solely as a brace.

CONCLUSION

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A therapeutic device for use on a length of a leg of a user, said length including an upper leg portion, a lower leg portion, a knee intermediate the upper leg portion and the lower leg portion, said leg length also defining opposing medial and lateral sides each extending the length of said leg length, said leg having an anterior, said device comprising:
    (a) a proximal framework portion configured for directly or indirectly supporting the upper leg portion, said proximal framework portion including a leg facing portion configured to be directed towards and generally facing said upper leg portion;
    (b) a distal framework portion configured for operatively engaging the lower leg portion, said distal framework portion including a leg facing portion configured to be directed towards and generally facing said lower leg portion, the distal framework portion including a first end proximate said knee and a second end more distal to said knee than the first end;
    (c) one or more distal framework engaging members operatively coupled to the distal framework portion, said one or more distal framework engaging members configured for operatively engaging the distal framework portion with the lower leg portion;
    (d) at least one operative connection intermediate to and operatively connecting said proximal and distal framework portions, said at least one operative connection configured to facilitate manipulation of said distal framework portion relative to said proximal framework portion in device flexion when said device is directly or indirectly supporting said leg and when said leg is in flexion; and
    (e) an extension assistor directly or indirectly attached, at one end, to the proximal framework portion and, at the other end, operatively coupled to the distal framework portion at a position closer to the first end of the distal framework portion than to the second end, thereby forming a bridging framework between the proximal framework portion and the distal framework portion such that at least a portion of the extension assistor is suspended above at least a portion of the proximal framework portion, the extension assistor configured to provide an urging force to the distal framework portion at a position closer to the at least one operative connection than to any of the one or more distal framework engaging members, wherein said extension assistor is configured to selectively discourage device flexion of said proximal and distal framework portions relative to one another, and, when activated, said extension assistor selectively encourages device extension of said proximal and distal framework portions relative to one another, thereby causing said leg to be urged into extension.

2. The therapeutic device of claim 1, wherein the extension assistor comprises an elongate tensile connector.

3. The therapeutic device of claim 2, wherein the extension assistor includes a ratchet element configured to take up a length of the elongate tensile connector.

4. The therapeutic device of claim 1, wherein the one or more proximal framework securing members comprises one or more straps configured to be placed in tension.

5. The therapeutic device of claim 1, wherein the therapeutic device further comprises:
    an inflatable proximal bladder adapted to be positioned between an anterior portion of the upper leg portion and at least one of the one or more proximal framework engaging members; and
    wherein the inflatable proximal bladder is configured to interact with the upper leg portion and the at least one of the one or more proximal framework securing members such that inflation of the inflatable proximal bladder while the extension assistor is connected causes the leg to be urged into extension due to the pushing of the inflatable proximal bladder against the upper leg portion and the at least one of the one or more proximal framework securing members.

6. The therapeutic device of claim 5, wherein the at least one of the one or more proximal framework engaging members comprises an elastic strap adapted to be in contact with an anterior side of the upper leg portion at approximately a same length at which the inflatable proximal bladder is in contact to the upper leg portion.

7. A method of therapeutic treatment of a knee comprising the steps of:
    (a) providing a therapeutic device for use on a length of a leg of a user, the therapeutic device having:
        (i) a proximal framework portion configured for directly or indirectly supporting the upper leg portion, said proximal framework portion including a leg facing portion configured to be directed towards and generally facing said upper leg portion;
        (ii) a distal framework portion configured for operatively engaging the lower leg portion, said distal framework portion including a leg facing portion configured to be directed towards and generally facing said lower leg portion, the distal framework portion including a first and proximate said knee and a second end more distal to said knee than the first end;
        (iii) one or more distal framework engaging members operatively coupled to the distal framework portion, said one or more distal framework engaging members configured for operatively engaging the distal framework portion with the lower leg portion;
        (iv) at least one operative connection intermediate to and operatively connecting said proximal and distal framework portions, said at least one operative connection configured to facilitate manipulation of said proximal and distal framework portions in device flexion when said device is engaging said leg and when said leg is in flexion; and
        (v) an extension assistor directly or indirectly attached, at one end, to the proximal framework portion and, at the other end, operatively coupled to the distal framework portion at a position closer to the first end of the distal framework portion than to the second end, thereby forming a bridging framework between the proximal framework portion and the distal framework portion, such that at least a portion of the extension assistor is suspended above at least a portion of the proximal framework portion, the extension assistor configured to provide an urging force to the distal framework portion at a position closer to the at least one operative connection than to any of the one or more distal framework engaging members, wherein said extension assistor is configured to selectively discourage device flexion of said proximal and distal framework portions relative to one another, and, when activated, said extension assistor selectively encourages device extension of said proximal and distal framework portions relative to one another, thereby causing said leg to be urged into extension;

(b) attaching the lower leg portion of the user with the distal framework portion using one or more distal framework engaging members; and (c) urging the leg into extension by activating the extension assistor to encourage extension of the proximal and distal framework portions relative to one another.

8. The therapeutic device of claim 1, wherein the extension assister defines a load path through the extension assister and between the proximal framework portion and the distal framework portion, and wherein the extension assister is configured to encourage device extension by changing a length of the load path.

9. The method of claim 7, wherein the extension assistor defines a load path through the extension assistor and between the proximal framework portion and the distal framework portion, and wherein the extension assister is configured to encourage device extension by changing a length of the load path.

10. The therapeutic device of claim 1, wherein the anterior engaging member is configured to provide, during extension of the leg, anterior resistive support to the anterior of the leg of the user, and the posterior engaging member is configured to provide, during extension of the leg, posterior resistive support to the posterior of the leg, wherein the anterior resistive support and the posterior resistive support are opposing.

11. The therapeutic device of claim 10, wherein the extension assistor is fixed to the distal framework portion at the position closer to the at least one operative connection than to any of the one or more distal framework engaging members.

12. The therapeutic device of claim 1, wherein the proximal framework portion defines a posterior side and an anterior side separated by a proximal anteromedian plane, the leg facing portion on the anterior side of the proximal framework portion configured to be directed towards and generally facing an anterior of the upper leg portion, and wherein the extension assistor is entirely positioned on the anterior side of the proximal anteromedian plane.

13. The therapeutic device of claim 1, wherein the distal framework portion defines a posterior side and an anterior side separated by a distal anteromedian plane, the leg facing portion on the anterior side of the distal framework portion configured to be directed towards and generally facing an anterior of the lower leg portion, and wherein the extension assistor is entirely positioned on the anterior side of the distal anteromedian plane.

* * * * *